(12) United States Patent
Urano et al.

(10) Patent No.: US 10,788,478 B2
(45) Date of Patent: Sep. 29, 2020

(54) BLOOD TEST KIT, MEMBER THEREOF, AND METHOD FOR MANUFACTURING THE SAME

(71) Applicant: FUJIFILM Corporation, Tokyo (JP)

(72) Inventors: Hikaru Urano, Ashigarakami-gun (JP); Haruyasu Nakatsugawa, Ashigarakami-gun (JP); Susumu Osawa, Tokyo (JP); Shinya Sugimoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 189 days.

(21) Appl. No.: 15/861,875

(22) Filed: Jan. 4, 2018

(65) Prior Publication Data
US 2018/0128808 A1 May 10, 2018

Related U.S. Application Data (63) Continuation of application No. PCT/JP2016/070009, filed on Jul. 6, 2016.

(30) Foreign Application Priority Data

Jul. 6, 2015 (JP) .................................. 2015-135065
Jul. 6, 2016 (JP) .................................. 2016-133958

(51) Int. Cl.
*G01N 33/49* (2006.01)
*A61B 5/15* (2006.01)
(Continued)

(52) U.S. Cl.
CPC ....... *G01N 33/49* (2013.01); *A61B 5/150022* (2013.01); *A61B 5/150206* (2013.01);
(Continued)

(58) Field of Classification Search
CPC .... G01N 33/49; G01N 33/487; G01N 33/483; G01N 33/48; A61B 5/150206; A61B 5/150007; A61B 5/15; A61B 5/150343
(Continued)

(56) References Cited

U.S. PATENT DOCUMENTS 6,471,868 B1 10/2002 Ito et al.
2001/0055784 A1 12/2001 Noda et al.
(Continued)

FOREIGN PATENT DOCUMENTS

| EP | 2 676 606 A1 | 12/2013 |
|----|--------------|---------|
| JP | 11-347017 A  | 12/1999 |

(Continued)

OTHER PUBLICATIONS

Kyowa Medex Co., Ltd., WO 03/005039 A1, English Machine Translation, obtained by STIC at the USPTO, obtained on Sep. 18, 2019, pp. 1-69. (Year: 2019).*

(Continued)

*Primary Examiner* — Christine T Mui
(74) *Attorney, Agent, or Firm* — Sughrue Mion, PLLC (57) ABSTRACT

An object is to perform analysis of a target component contained in a small volume of blood sample at high accuracy using a normal component homeostatically present in blood. Provided is a blood test kit for analyzing a concentration of a target component in a blood sample by using a normal component homeostatically present in blood, the kit including: a diluent solution for diluting a blood sample; and a member selected from the group consisting of a first storing instrument in which the diluent solution is stored, a separating instrument for separating and recovering blood plasma from the blood sample diluted with the diluent solution, a holding instrument for holding the separating instrument, a second storing instrument for storing the
(Continued)

recovered blood plasma, and a sealing instrument for keeping the stored blood plasma in the second storing instrument, in which an amount of the normal component which is derived from the member and may be contained in the diluent solution is defined.

8 Claims, 2 Drawing Sheets

(51) Int. Cl.
  *G01N 1/10* (2006.01)
  *G01N 33/96* (2006.01)
  *G01N 33/48* (2006.01)
  *B01L 3/00* (2006.01)
  *G01N 1/38* (2006.01)
  *G01N 33/66* (2006.01)

(52) U.S. Cl.
  CPC .. *A61B 5/150343* (2013.01); *A61B 5/150755* (2013.01); *B01L 3/502* (2013.01); *G01N 1/10* (2013.01); *G01N 33/48* (2013.01); *G01N 33/491* (2013.01); *G01N 33/96* (2013.01); *A61B 5/150351* (2013.01); *B01L 2200/16* (2013.01); *B01L 2300/047* (2013.01); *B01L 2300/049* (2013.01); *B01L 2300/0681* (2013.01); *B01L 2300/0832* (2013.01); *B01L 2300/0867* (2013.01); *G01N 1/38* (2013.01); *G01N 33/66* (2013.01)

(58) Field of Classification Search
  USPC ....................................... 436/10, 8; 422/430
  See application file for complete search history.

(56) References Cited

U.S. PATENT DOCUMENTS

| | | | |
|---|---|---|---|
| 2002/0153316 | A1 | 10/2002 | Nanba et al. |
| 2003/0175167 | A1 | 9/2003 | Takanori et al. |
| 2004/0141888 | A1 | 7/2004 | Nanba et al. |
| 2005/0232813 | A1 | 10/2005 | Karmali |
| 2011/0020195 | A1* | 1/2011 | Luotola ............. A61B 10/0045 422/512 |
| 2016/0011150 | A1* | 1/2016 | Onuma ............ G01N 27/44791 204/451 |

FOREIGN PATENT DOCUMENTS

| | | | | |
|---|---|---|---|---|
| JP | 2000-254461 | A | | 9/2000 |
| JP | 2001-330603 | A | | 11/2001 |
| JP | 2003-161729 | A | | 6/2003 |
| JP | 2003-270239 | A | | 9/2003 |
| JP | 2009-109196 | A | | 5/2009 |
| JP | 2009-122082 | A | | 6/2009 |
| JP | 2011-112451 | A | | 6/2011 |
| JP | 2014-141829 | * | 7/2014 | .......... G01N 27/447 |
| WO | 03/005039 | A1 | | 1/2003 |
| WO | WO 2003/005039 | * | 1/2003 | ............. G01N 33/72 |
| WO | 2011/065212 | A1 | | 6/2011 |
| WO | WO 2011/065212 | * | 6/2011 | ............. G01N 33/48 |

OTHER PUBLICATIONS

Osawa et al, WO 2011/065212, English Machine Translation, obtained by STIC at USTPO, obtained on Sep. 18, 2019, pp. 1-20. (Year: 2019).*
Communication dated Mar. 21, 2019, from the State Intellectual Property Office of People's Republic of China in counterpart Chinese Application No. 201680039462.1.
Office Action dated May 20, 2019 issued in the corresponding Korean patent application No. 10-2018-7000463.
Extended European Search Report dated Jul. 12, 2018 from the European Patent Office in counterpart European application No. 16821433.6.
Horita, M., et al., "Establishment of Mail Medical Examination System Using Immediate Plasma Separating Device by the Self-Collection Blood: The Method of Dilution Ratio Calculation by Using Internal Standard for the Sample with Different Amount of Collecting Blood", Japanese Journal of Clinical Pathology, vol. 56, No. 7, 2008, XP009503400, 39 pages.
Notification of Reasons for Refusal, dated Sep. 4, 2018, issued in corresponding Japanese Application No. 2016-133958, 4 pages in English and Japanese.
Susumu Osawa et al., "Revolution of medical services at home using a small amount of blood collected from the fingertip", Clinical Testing, May 15, 2015, vol. 59, No. 5, pp. 397-404.
International Search Report dated Oct. 11, 2016 issued by the International Searching Authority in International Application No. PCT/JP2016/070009.
Written Opinion dated Oct. 11, 2016 issued by the International Searching Authority in International Application No. PCT/JP2016/070009.
International Preliminary Report on Patentability dated Aug. 3, 2017 in International Application No. PCT/JP2016/070009.
Yan Lu-wen, Ed., "Photovoltaic Technology and Applications", Apr. 2015, p. 58, 3 pages total.
Office Action dated Sep. 27, 2019 in corresponding Chinese Application No. 201680039462.1.
Communication dated Mar. 18, 2020 from the State Intellectual Property Office of the P.R.C. in Chinese Application No. 201680039462.1.

* cited by examiner

BLOOD TEST KIT, MEMBER THEREOF, AND METHOD FOR MANUFACTURING THE SAME

CROSS-REFERENCE TO RELATED APPLICATIONS

This application is a Continuation of PCT International Application No. PCT/JP2016/070009 filed on Jul. 6, 2016, which claims priority under 35 U.S.C. § 119(a) to Japanese Patent Application No. 2015-135065 filed on Jul. 6, 2015 and Japanese Patent Application No. 2016-133958 filed on Jul. 6, 2016. Each of the above application(s) is hereby expressly incorporated by reference, in its entirety, into the present application.

BACKGROUND OF THE INVENTION

1. Field of the Invention

The present invention relates to a blood test kit for analyzing a target component in a small volume of a blood sample, a member used for the kit, and a method for manufacturing the same.

2. Description of the Related Art

As blood collection, generally, there are general blood collection in which a qualified person such as a doctor collects blood from the vein using a syringe, and self-blood collection in which a subject to be tested pricks his finger and the like using a blood collection needle so as to collect blood.

The blood collected by the general blood collection is transported to a medical institution or a test institution in a sealed state in a blood collection container, and tests are performed therein. In a case where the blood is transported without separating blood cells and blood plasma, tests are performed after a medical institution or a test institution performs centrifugation to separate the blood into blood cells and blood plasma. In addition, in the self-blood collection which is performed by a subject to be tested, the collected blood is separated into blood cells and blood plasma by a separation membrane, and the blood is transported to a test lab in a separated state, and then tests are performed therein.

JP2003-161729A discloses a method for testing a blood sample collected by self-blood collection, and specifically discloses a method for quantitatively determining a component to be quantitatively determined in a biological specimen, the method including 1) step of preparing a specimen for quantitation consisting of an unknown volume of a biological specimen containing a component to be quantitatively determined which is collected without quantitatively determining the volume thereof, and a certain volume of an aqueous solution containing a certain amount of an indicator substance, 2) step of obtaining a dilution factor (a) of the biological specimen from a concentration ($C_1$) of the indicator substance in the aqueous solution of a certain volume which contains a certain amount of the indicator substance, and a concentration ($C_2$) of the indicator substance in the specimen for quantitation, 3) step of obtaining a concentration (Y) of the component to be quantitatively determined in the specimen for quantitation, and 4) step of determining the component to be quantitatively determined in the biological specimen from the dilution factor (a) of the biological specimen obtained in 2), and the concentration (Y) of the substance to be quantitatively determined in the specimen for quantitation obtained in 3).

JP2001-330603A discloses a quantitative analysis method in which an amount of a target component to be analyzed in a sample is measured, an amount of a normal component originally and homeostatically present in the sample, other than the target component, is measured, a volume of the sample is determined from the amount of this normal component and a known concentration of the normal component in the sample, and therefore a concentration of the target component to be analyzed in the sample is determined from the volume of the sample and the amount of the target component to be analyzed.

In addition, JP2009-122082A discloses that a small volume of blood is collected from a human or an animal using a blood dilution quantitative instrument, and after dilution of the blood, or without dilution, a certain volume thereof is supplied to another instrument or container or is directly supplied to a reagent. Furthermore, JP2009-109196A discloses a method for quantitatively determining a concentration of a component to be quantitatively determined in a biological specimen by utilizing an absorbance of an indicator substance in an aqueous solution for dilution.

At present, a method in which an indicator substance disclosed in JP2003-161729A, so called an external standard substance is used is employed in commercially available blood test kits.

SUMMARY OF THE INVENTION

In the method disclosed in JP2003-161729A, it is required that a ratio of a diluent solution to a blood sample volume is set high in a case of a small volume of a blood sample. In this case, a change rate in a volume of a diluent solution before and after diluting the blood sample becomes very small, and a change rate in a concentration of an internal standard substance becomes small, and therefore there is a problem that a level of repeatability and reproducibility with respect to measurement values decreases.

JP2001-330603A discloses that about 100 µL it of whole blood of a healthy subject is added dropwise to a porous membrane, blood cells are separated to develop serum, and thereafter, 150 µL of a physiologically isotonic solution, PBS (phosphate-buffered saline: pH 7.4) is added thereto, and the supernatant obtained by centrifuging the obtained solution is analyzed as an analytical specimen, but does not disclose collection of blood of less than 100 µL.

In the method of JP2009-122082A, a blood volume of 10 µL is accurately collected with a micropipette so as to be analyzed, but in a case where the blood is collected by a patient who lacks experience in blood collection, it is difficult to accurately collect a certain volume thereof, and therefore a case in which tests are performed with blood collection including errors will result in measurement values including the errors.

The method disclosed in JP2009-109196A is the measurement with a dilution factor of about 10, and in a case where the dilution factor is further increased to sufficiently secure a volume of diluted blood, there is a problem that a level of repeatability and reproducibility with respect to measurement values decreases, as same as in JP2003-161729A.

As described above, a blood analysis method in which a high level of repeatability and reproducibility is achieved with respect to measurement values in a case of using a small volume of a blood sample, is desired. The inventors of the present invention have examined a method in which an external standard substance is used in consideration that use of an internal standard substance, which has been proposed in the related art, is not sufficient for performing analysis at high accuracy.

An object of the present invention is to provide a blood test kit for quantitatively analyzing a component by precisely obtaining a dilution factor, at accuracy not described in the related arts of, for example, JP2003-161729A and JP2001-330603A by defining a concentration of a normal component homeostatically present in blood, which is eluted from a member of the blood test kit into a buffer solution in a method for analyzing a concentration of a target component in a blood sample by using a normal component homeostatically present in blood as a method for quantitatively analyzing a component by diluting a small volume of blood with a buffer solution. In addition, a blood test kit capable of further improving the accuracy by using a method for obtaining a dilution factor with an internal standard in combination is provided.

As a result of intensive studies to solve the object described above, the inventors of the present invention have found that the object described above can be solved by suppressing an amount of the normal component derived from a member to be a certain amount or less in a blood analysis method in which a collected blood sample is diluted with a diluent solution, a dilution factor is determined by using a normal value of the normal component which is homeostatically present in blood, and a concentration of a target component in the blood sample is analyzed, and therefore have completed the present invention. The present invention provides the following inventions.

[1] A blood test kit for analyzing a concentration of a target component in a blood sample by using a normal component homeostatically present in blood, the kit comprising: a diluent solution for diluting the blood sample; and a member selected from the group consisting of a first storing instrument in which the diluent solution is stored, a separating instrument for separating and recovering blood plasma from the blood sample diluted with the diluent solution, a holding instrument for holding the separating instrument, a second storing instrument for storing the recovered blood plasma, and a sealing instrument for keeping the stored blood plasma in the second storing instrument, in which an amount of the normal component which is derived from the member and may be contained in the diluent solution is defined.

[2] The blood test kit according to 1, in which an amount of the normal component which is derived from the member and may be contained in the diluent solution is 0.5% by mass or less with respect to the amount of the diluent solution.

[3] The blood test kit according to 1 or 2, in which a volume of the diluent solution is 15 times or smaller a volume of blood plasma.

[4] The blood test kit according to any one of 1 to 3, in which the normal component which is homeostatically present in blood is sodium ions or chloride ions.

[5] The blood test kit according to any one of 1 to 4, in which the normal component which is homeostatically present in blood is sodium ions or chloride ions, and another normal component which is homeostatically present in blood.

[6] The blood test kit according to 5, in which the other normal component is total protein or albumins.

[7] The blood test kit according to any one of 1 to 6, in which analysis of a concentration of a target component of the blood sample is verified by using the other normal component which is homeostatically present in blood.

[8] The blood test kit according to any one of 1 to 7, in which the member included in the blood test kit has a separating instrument for recovering blood plasma from the blood sample diluted with the diluent solution.

[9] The blood test kit according to any one of 1 to 8, in which the diluent solution does not contain the normal component which is homeostatically present in blood.

[10] The blood test kit according to any one of 1 to 9, in which the diluent solution contains an amino alcohol compound selected from the group consisting of 2-amino-2-methyl-1-propanol, 2-ethylaminoethanol, N-methyl-D-glucamine, diethanolamine, and triethanolamine, and contains a buffering agent selected from the group consisting of 2-[4-(2-hydroxyethyl)-1-piperazinyl] ethanesulfonic acid also called HEPES, N-tris(hydroxymethyl)methyl-2-aminoethanesulfonic acid also called TES, 3-morpholinopropanesulfonic acid also called MOPS, and N,N-bis(2-hydroxyethyl)-2-aminoethanesulfonic acid also called BES.

[11] The blood test kit according to any one of 1 to 10, in which the diluent solution further contains a normal component not present in blood.

[12] The blood test kit according to 11, in which the normal component not present in blood is lithium ions or glycerol 3-phosphate.

[13] A member which is used for the blood test kit according to any one of 1 to 12.

[14] The member according to 13, in which the member is a member selected from the group consisting of the a storing instrument in which a diluent solution is stored, a separating instrument for separating and recovering blood plasma from a blood sample diluted with the diluent solution, a holding instrument for holding the separating instrument, a second storing instrument for storing the recovered blood plasma, and a sealing instrument for keeping the stored blood plasma in the second storing instrument.

[15] A method for manufacturing the blood test kit according to any one of 1 to 12, or the member according to 13 or 14, the method comprising: a step of washing the member under a condition effective for removing a normal component which is homeostatically present in blood.

[16] The manufacturing method according to 15, in which the condition is use of water having an electric conductivity of 1 µS/cm or less.

According to a blood test kit and a member thereof of the present invention, a concentration of a target component in a blood sample can be analyzed at high accuracy by using a normal component which is homeostatically present in blood.

According to a manufacturing method of the present invention, it is possible to provide the blood test kit and the member thereof by which the above-described analysis can be performed at high accuracy.

DESCRIPTION OF THE PREFERRED EMBODIMENTS

Hereinafter, an embodiment of the present invention will be described.

A range indicated by X to Y includes values of an upper limit X and a lower limit Y. A normal component homeostatically present in blood may be referred to as an external standard substance or an external standard. In addition, a normal component not present in blood may be referred to as an internal standard substance or an internal standard.

As a method of collecting a small volume of blood, a method of performing blood analysis using a filter paper is disclosed in JP1998-104226A (JP-H10-104226A). Furthermore, a method of using a porous material having a high level of blood retention property instead of a filter paper is disclosed in JP2001-330603A. In these methods, it is described that in order to extract blood components absorbed in the material with a buffer solution and the like and measure the components, sodium ions, chloride ions, calcium ions, protein, and the like which are external standard substances homeostatically present in the blood are used as a reference substance for estimating a dilution ratio by a buffer solution in a case where blood is eluted and redissolved. In these methods, a volume of blood collection varies, and if a dilution ratio of the collected blood becomes high, the accuracy of analysis thereafter decreases, and thus the result varies. Because the blood is once coagulated and solidified, the stability of the target component to be analyzed is not sufficiently secured in some cases. In addition, as a buffer solution for extracting a biological component from a dried specimen, it is necessary to use a buffer solution to which NaOH, NaCl, or HCl is added in order to adjust the pH and stabilize the biological component. Therefore, there was a problem that concentrations of sodium ions and chloride ions which are present at a relatively high concentration, are homeostatic components in the specimen, and have little difference between individuals, cannot be used as an external standard, which is for correcting a concentration of another biological component of the diluted specimen.

Meanwhile, a method is disclosed in JP2003-161729A as a method for diluting a small volume of the collected blood with a buffer solution containing an internal standard and quantitatively determining an unknown amount of components present in the diluted blood plasma from a dilution factor of the internal standard substance. N-(2-hydroxy-3-sulfopropyl)-3,5-dimethoxyaniline sodium salt (HSDA) or acid blue 9 (brilliant blue FCF) is used as an internal standard substance, and a buffering agent and a preservative are used for stably maintaining blood. Such a formulation realized maintaining the stability of the components thereof by not coagulating the blood, but in a case where a volume of blood collection varies and a collection volume is small, there still were problems that a dilution ratio of an internal standard substance after dilution becomes small, and the reliability of test accuracy deteriorates as an amount of blood components itself decreased. In addition, in the method of diluting with a buffer solution, a biological component is stored in a buffer solution at physiological conditions of pH 7.4, and thus is excellent in stability during transportation, but because a specimen is added to a buffer solution to which an internal standard was added, a dilution ratio of the internal standard is small, and there is a problem that with addition of only a small amount of the specimen, a measurement error is likely to occur.

In examples of these related arts, a phosphate buffered saline is used in a buffer solution for extraction because of excellence in maintaining the stability of a biological component, but the phosphate buffered saline contains sodium ions or chloride ions. Therefore, sodium ions or chloride ions cannot be used as an external standard, and calcium ions, proteins, and the like are used. Accordingly, in order to perform a blood test with a small volume of the blood at high accuracy, use of an external standard substance for correcting a dilution ratio disclosed in the related art and use of a buffer solution containing an internal standard substance disclosed in the related art were not sufficient for ensuring test accuracy.

Although being homeostatic substances in the blood, in sodium ions for example, a distribution width of a normal value is 134 to 146 mmol/L, and therefore it is necessary to more accurately calculate a dilution factor. A decrease of the accuracy of a dilution factor affects a bad influence on the test accuracy, and therefore a risk of deteriorating the reliability of a test increases. Particularly, in a case where there is only a little contamination due to an external standard substance eluted from a member constituting a kit into a buffer solution, if a volume of blood collection is large or small, a degree of influence of the contamination on the calculation of a dilution factor varies. JP2001-330603A does not all mention about maintaining constant such a degree of influence of the contamination of an external standard substance eluted from a member constituting a kit into a buffer solution, on the calculation of a dilution factor.

In addition, JP2003-161729A discloses about an internal standard, but does not disclose the use of an external standard in combination. Accordingly, there is no disclosure regarding the contamination of the external standard, and a specific means for preventing the contamination is not proposed at all.

An object of the present invention is to provide a blood test kit for analyzing a concentration of a target component by diluting a small volume of a blood sample with a buffer solution, by which a dilution factor can be obtained at accuracy not described in the related art in a case where analysis of a control component is performed by using an external standard homeostatically present in blood. In a means for solving the above, an amount of the above-described normal component which is derived from the above-described member and may be contained in the diluent solution is defined. In addition, in a preferred embodiment, not only an external standard but also an internal standard is used.

According to the present invention, in a method for measuring a component to be analyzed in blood, when a small volume of blood components is added to a diluent solution so as to be diluted in a case where a patient collects blood by himself, a member which constitutes a kit and is made of a synthetic resin (in the present specification, plastic is used synonymously with the synthetic resin), glass, or rubber is washed in advance, and by suppressing elution of a homeostatic normal component from the member constituting the kit as much as possible, a homeostatic normal component derived from blood is detected at sufficiently high accuracy. Therefore, it is possible to realize a measuring method in which a component to be analyzed can be quantitatively determined at high accuracy, or a blood test system in which the measuring method is used.

In addition, a blood test kit capable of further improving the accuracy by further using a method for obtaining a dilution factor with an internal standard in combination is provided.

[1] Blood Test Kit

A blood test kit for analyzing a concentration of a target component in a blood sample by using a normal component homeostatically present in blood is a blood test kit which includes a diluent solution for diluting the blood sample; and a member selected from the group consisting of a first storing instrument in which the diluent solution is stored, a separating instrument for separating and recovering blood plasma from the blood sample diluted with the diluent solution, a holding instrument for holding the separating instrument, a second storing instrument for storing the recovered blood plasma, and a sealing instrument for keeping the stored blood plasma in the second storing instrument, and which is characterized to define an amount of the normal component which is derived from the member and may be contained in the diluent solution.

Analysis of a concentration of a target component in a blood sample includes determining a concentration of a target component (that is, quantitatively determining a target component), determining whether a concentration of a target component is equal to or higher than a predetermined reference value or equal to or lower than a predetermined reference value, and the like, and an embodiment of the analysis is not particularly limited.

[Method and Volume of Blood Collection]

The blood test kit of the present invention is used for collecting a blood sample. The collection of blood by the blood test kit of the present invention may be performed by a subject to be tested or by a qualified person such as a doctor.

In a preferred embodiment, a patient himself pricks a fingertip and the like using a blade-attached instrument such as a lancet and then collects the blood flowing out of the skin. It is preferable that the blood is collected in a manner of reducing the invasiveness so as to alleviate the burden on a patient, and when collecting the blood, it is desirable to be able to collect the blood with little pain or painlessly. In this case, it is desired that a depth and a size of the wound are small, by which a volume of blood that can be collected is very small. Accordingly, a volume of a sample collected by the blood test kit of the present invention (that is, a volume of the collected blood) is preferably 100 µL or less. In the present invention, even with such a small volume of blood collection of a patient, it is possible to define a concentration of the normal component which is homeostatically present in blood and may be released from the member of the blood test kit to the diluent solution to be low, and to provide a method for measuring a component to be analyzed at high measurement accuracy by using, for example, sodium ions or chloride ions as a normal component homeo statically present in blood.

[Normal Component Homeostatically Present in Blood]

As above, in a method in which a target component after diluting blood plasma of which a dilution factor of blood plasma components is high, is obtained from a change rate of a concentration of a substance present in the diluent solution beforehand, in order to precisely analyze a concentration of blood plasma present in the blood before dilution, a change rate in concentration is extremely small, which leads to adverse effects that measurement error becomes high and reproducibility of measurement deteriorates. Accordingly, the blood test kit of the present invention is the blood test kit for analyzing a concentration of a target component in a blood sample by using a normal component which is homeostatically present in blood.

The phrase "by using" a normal component means that a dilution factor for analyzing a concentration of a target component is determined based on a normal value (homeostatic value) of the normal component. Accordingly, the analysis of a concentration of a target component in a blood sample by using a normal component homeostatically present in blood also means that a concentration of a target component is analyzed by determining a dilution factor based on a normal value (homeostatic value) of the normal component homeostatically present in blood.

Examples of the normal component which is homeostatically present in the blood include sodium ions, chloride ions, potassium ions, magnesium ions, calcium ions, total protein, albumins, and the like. As a concentration of these normal components contained in serum and blood plasma of the blood sample, a concentration of sodium ions is 134 to 146 mmol/L (average value: 142 mmol/L), a concentration of chloride ions is 97 to 107 mmol/L (average value: 102 mmol/L), a concentration of potassium ions is 3.2 to 4.8 mmol/L (average value: 4.0 mmol/L), a concentration of magnesium ions is 0.75 to 1.0 mmol/L (average value: 0.9 mmol/L), a concentration of calcium ions is 4.2 to 5.1 mmol/L (average value: 4.65 mmol/L), a concentration of total protein is 6.7 to 8.3 g/100 mL (average value: 7.5 g/100 mL), and a concentration of albumins is 4.1 to 5.1 g/100 mL (average value: 4.6 g/100 mL). The present invention is for enabling measurement of a target component in a case where a volume of blood to be collected is extremely small for alleviating patient's pain. In a case where a small volume of blood is diluted with a diluent solution, it is required that a concentration of "the normal component homeostatically present in the blood", which is present in the diluent solution is accurately measured. As a dilution factor becomes high, a concentration of a component, which is originally present in the blood, in the diluent solution decreases, and depending on a dilution factor, there is a possibility that measurement error is included when measuring the concentration. Accordingly, it is preferable to measure the normal component present at a high concentration in a small volume of the blood so as to detect the normal component at sufficiently high accuracy when a small volume of the blood components is diluted at a high dilution factor. In the present invention, it is preferable to use sodium ions ($Na^+$) or chloride ions ($Cl^-$) which are present at a high concentration among the components homeostatically present in the blood sample. Furthermore, it is most preferable to measure sodium ions which are present in the blood at a highest amount among the normal components homeostatically present in the blood described above. Regarding sodium ions, an average value represents a normal value (median value of the reference range), and this value is 142 mmol/L, accounting for 90 mole % or more of total cations in the blood plasma.

An occupancy rate of blood plasma components in the blood of a subject to be tested is about 55% in terms of a volume ratio, but the ratio varies depending on changes in salt intake of the subject, and the like. Therefore, in a case of using the kit of the present invention, a dilution factor of blood plasma is determined by using a normal value of the normal component which is homeostatically present in blood plasma, and a concentration of a target component in blood plasma in a blood sample is analyzed by using the determined dilution factor. As a method for determining a dilution factor, it is possible to obtain a dilution factor by calculating a dilution factor (Y/X) of the blood plasma components in a blood sample from a measurement value (concentration X) of an external standard substance (for example, sodium ions and the like) in a diluent solution of the blood plasma, and a known concentration value (concentration Y; in a case of sodium ions, 142 mmol/L) of the external standard substance (for example, sodium ions and the like) contained in blood plasma of the blood sample. Using this dilution factor, a value (concentration Z) of a target component in a diluent solution of the blood plasma is measured, and by multiplying this measurement value by the dilution factor, it is possible to measure a concentration [Z×(Y/X)] of a target component to be analyzed actually contained in blood plasma of the blood sample.

A concentration of sodium ions and a concentration of chloride ions can be measured by, for example, the flame photometric method, the glass-electrode method, the titration method, the ion selective electrode method, the enzyme activity method, and the like.

In a case of measuring sodium ions, it is possible to use an enzymatic assay by which sodium ions in several µL of a specimen of very low sodium concentration (24 mmol/L or less) diluted with a diluent solution are measured by utilizing that the enzyme activity of the enzyme galactosidase is activated by sodium ions. This method can be applied to a biochemical/automated immunoassay analyzer, and is highly efficient and economical for not required of another measuring instrument for sodium ions measurement.

In addition, in order to confirm whether the blood test kit in which an amount of a normal component derived from the member is defined is actually used, or whether a method for diluting blood and recovering blood plasma is normally performed, it is preferable that an additional dilution factor is separately obtained from the other normal component in blood plasma to check whether values thereof match with the dilution factor obtained above. The term "match" means, with respect to two measurement values (a, b), a ratio of their differences to their average values, that is, |a−b|/{(a+b)/2}×100 is 20% or smaller, preferably 10% or smaller, and more preferably 5% or smaller. Accordingly, it is possible to verify that the analysis of a concentration of a target component in a blood sample is normally performed. Examples of the normal component homeostatically present in the blood plasma, which is other than sodium ions and chloride ions are preferably selected from total protein or albumins, and it is more preferable that the component is total protein. Examples of a method for measuring total protein include the known method such as the biuret method, the ultraviolet absorption method, the Bradford method, the Lowry method, the bicinchoninic acid (BCA) method, and the fluorescence method, and it is possible to select a method to be used appropriately depending on characteristics, sensitivity, specimen amount, and the like of a measurement specimen.

[Normal Component Not Present in Blood]

As a preferred embodiment, the kit is for analyzing a concentration of a target component in a blood sample by using a normal component not present in blood together with a normal component homeostatically present in blood.

It is possible to use the normal component not present in blood by adding a predetermined concentration of the normal component in the diluent solution (to be described later) of the kit. As the normal component not present in blood, it is possible to use a substance which is not contained in the blood sample at all, or is contained thereto but in an ultra-small amount. As the normal component not present in blood, it is preferable to use substances which do not interfere with the measurement of the target component in the blood sample, substances which do not decompose under the action of biological enzymes in the blood sample, substances which are stable during dilution, substances which do not pass through a blood cell membrane and not contained in the blood cells, substances which are not adsorbed to a storing container of the diluent solution, and substances which can be utilized by a detection system capable of measurement at high accuracy.

As the normal component not present in blood, a substance which is stable even if the substance is stored for a long period of time in a state of being added to the diluent solution, is preferable. Examples of the normal component not present in blood include glycerol 3-phosphate, Li, Rb, Cs, or Fr as alkali metal, and Sr, Ba, or Ra as alkaline earth metal. Among these, Li and glycerol 3-phosphate is preferable.

These normal components not present in blood can develop color by adding a second reagent at the time of measuring a concentration after blood dilution, and the concentration in the diluted blood can be obtained from color optical density. For example, regarding the measurement of lithium ions added to the diluent solution, a large number of specimens of a small amount can be easily measured by the chelate colorimetric method (halogenated porphyrin chelating method: perfluoro-5,10,15,20-tetraphenyl-21H,23H-porphyrin) using an automatic biochemistry analyzer.

By using the blood test kit for analyzing a concentration of a target component of the blood sample, in which a normal component not present in blood is used together with a normal component homeostatically present in blood, that is, two normal components are used in combination, it is possible to realize the analysis having higher reliability.

In the embodiment in which two normal components are used in combination, sodium ions are used as a normal component homeostatically present in blood and lithium ions are used as a normal component not present in blood, and in a case where sodium ions measurement is carried out by the enzyme activity method utilizing that β-galactosidase activity is in a proportional relationship, and lithium ions measurement is carried out by the above-described chelate colorimetric method, a dilution factor of the blood sample can be calculated by any one of Formulas 1 to 4.

$$X=(A+C)/(B+D) \quad \text{Formula 1:}$$

$$X=\{(A^2+C^2)^{1/2}\}/\{(B^2+D^2)^{1/2}\} \quad \text{Formula 2:}$$

$$X=a\times(B+D)\pm b \quad \text{Formula 3:}$$

(a and b are coefficients, and a standard curve represented by Formula 3 is prepared in advance by acquiring data of (B+D) and a dilution factor)

$$X=A/B' \ (B'=(A\times D)/C) \quad \text{Formula 4:}$$

In the above formulas, A, B, C, D, B', and X are defined as follows.
A: Absorbance in a case of coloring a buffer solution
B: Absorbance change after adding blood plasma
C: Absorbance at a median value of 142 mmol/L of blood plasma sodium
D: Absorbance at a concentration of sodium ions after diluting blood plasma
B': Correction value of an absorbance of a normal component not present in the blood of diluted blood plasma obtained by a dilution factor calculated from an absorbance of blood plasma sodium
X: Dilution factor of blood plasma As another calculation method for a case of obtaining a dilution ratio, an aspect in which a dilution ratio is calculated by Formula 5 using the root-mean-square method, a concentration of a target component to be analyzed in a diluent solution is multiplied by the dilution ratio calculated by Formula 5, and therefore a concentration of a target component in the components in a blood sample is analyzed, is preferable.

$$X=[\{(A/B)^2+(C/D)^2\}/2]^{1/2} \quad \text{Formula 5:}$$

A concentration of a target component in the components of the blood sample can be calculated from a concentration of a target component of the diluent solution based on the above dilution factor.

[Diluent Solution]

The blood test kit of the present invention includes the diluent solution for diluting a collected blood sample. The diluent solution for diluting a blood sample is a diluent solution which does not contain a normal component homeostatically present in the blood, which is used for obtaining a dilution factor. The phrase "does not contain" in the present specification means that the solution "substantially does not contain" the component. The phrase "substantially does not contain" means that the solution does not contain a homeostatic substance used for obtaining a dilution factor at all, or even if the homeostatic substance is contained, this means a case where an ultra-small amount of concentration is contained to the extent that does not affect measurement of a homeostatic substance in a diluent solution after diluting a blood sample. In a case where sodium ions or chloride ions are used as a normal component homeostatically present in blood, a diluent solution which substantially does not contain sodium ions or chloride ions is used as a diluent solution.

In the present invention, after a blood sample collected by a patient is diluted, it is possible to transport the sample to a medical institution or a test institution so that a concentration of a target component is analyzed. There is a possibility that a long period of time is taken from blood collection to analysis, and therefore during this time, it is preferable to prevent degradation or denaturation of a target component in a diluent solution of the blood. A pH of blood is generally maintained constant at a pH of about 7.30 to 7.40 for healthy subjects. Accordingly, in order to prevent degradation or denaturation of a target component, a diluent solution is preferably a buffer solution having a buffering action within a pH range of pH 6.5 to pH 8.0, preferably pH 7.0 to pH 7.5, and further preferably pH 7.3 to pH 7.4, and the diluting solution is preferably a buffer solution containing a buffering component for suppressing variation in pH.

As the type of the buffer solution, an acetate buffer solution (Na), a phosphate buffer solution (Na), a citrate buffer solution (Na), a borate buffer solution (Na), a tartrate buffer solution (Na), a Tris (tris(hydroxymethyl) aminoethane buffer solution (Cl), a HEPES ([2-[4-(2-hydroxyethyl)-1-piperazinyl]ethanesulfonic acid]) buffer solution, a phosphate buffered saline (Na), and the like are known. Among these, as a buffer solution having a pH around 7.0 to 8.0, the phosphate buffer solution, the Tris buffer solution, and the HEPES buffer solution are representative. However, the phosphate buffer solution contains a sodium salt of phosphoric acid, the Tris buffer solution has a dissociation pKa of 8.08, and thus is usually used in combination with hydrochloric acid for imparting buffering ability around pH 7.0 to pH 8.0, and a dissociation pKa of sulfonic acid of HEPES is 7.55, but in order to adjust buffer solution at constant ionic strength, a HEPES mixture of sodium oxide and sodium chloride is used. Therefore, these solutions are useful as a buffer solution having an action of maintaining pH constant, but contain sodium ions or chloride ions which are substances preferably used as an external standard substance in the present invention, and thus, application thereof to the present invention is not preferable.

As the diluent solution included in the kit of the present invention, it is preferable to use a buffer solution which does not contain sodium ions or chloride ions. The diluent solution used in the present invention is preferably a diluent solution including at least an amino alcohol compound selected from the group consisting of 2-amino-2-methyl-1-propanol (AMP), 2-ethylaminoethanol, N-methyl-D-glucamine, diethanolamine, and triethanolamine, and a buffering agent selected from the group consisting of 2-[4-(2-hydroxyethyl)-1-piperazinyl]ethanesulfonic acid (pKa=7.55) also called HEPES which is a buffering agent having a pKa around 7.4, N-tris(hydroxymethyl)methyl-2-aminoethanesulfonic acid also called TES (pKa=7.50), 3-morpholinopropanesulfonic acid also called MOPS (pKa=7.20), and N,N-bis(2-hydroxyethyl)-2-aminoethanesulfonic acid also called BES (pKa=7.15), which are Good's buffer solutions (Good's buffers). Among these, a combination of 2-amino-2-methyl-1-propanol (AMP) with HEPES, TES, MOPS, or BES is preferable, and a combination of 2-amino-2-methyl-1-propanol (AMP) with HEPES is most preferable.

For preparing the buffer solution described above, an amino alcohol may be mixed with the Good's buffer solutions at a concentration ratio of 1:2 to 2:1, preferably 1:1.5 to 1.5:1, and more preferably 1:1. A concentration of the buffer solution is not limited, but a concentration of the amino alcohol or the Good's buffer solution is 0.1 to 1000 mmol/L, preferably 1 to 500 mmol/L, and more preferably 10 to 100 mmol/L.

A chelating agent, a surfactant, an antibacterial agent, a preservative, a coenzyme, a saccharide, and the like may be contained in the buffer solution in order to keep a target component to be analyzed stable. Examples of the chelating agent include a salt of ethylenediaminetetraacetic acid (EDTA), citrate, oxalate, and the like. Examples of the surfactant include a cationic surfactant, an anionic surfactant, an amphoteric surfactant, and a nonionic surfactant. Examples of the preservative include sodium azide, antibiotics, and the like. Examples of the coenzyme include pyridoxal phosphate, magnesium, zinc, and the like. Examples of the saccharide of a red blood cell-stabilizing agent include mannitol, dextrose, oligosaccharide, and the like. Particularly, by adding the antibiotics, it is possible to suppress the growth of bacteria which are partially mixed from the surface of the finger at the time of collecting blood from the finger, suppress degradation of biological components by bacteria, and stabilize the biological components.

It is import that these diluent solutions do not contain a normal component homeostatically present in blood and an internal standard substance, and do not interfere with a measuring system. In addition, it is preferable that components diluted with these diluent solutions are not interfered even by various measuring methods using the biochemical/automated immunoassay analyzer, that blood cells are not hemolyzed, and that biological components can be stored stably even at 37° C.

In a case where whole blood is used for a blood sample, filtration of blood cell components in a diluted blood through a filter is required, and by setting osmotic pressure of the buffer solution equivalent to (285 mOsm/kg (mOsm/kg is an osmotic pressure that 1 kg of water of the solution has, and indicates millimoles of ions)) or higher than that of the blood, it is possible to prevent hemolysis. The osmotic pressure can be adjusted to be isotonic by measurement of a target component, salts which do not affect a normal component homeostatically present in the blood, sugars, buffering agents, and the like.

As a measurement method in which blood plasma sodium ions diluted with a diluent solution is used as a normal component homeostatically present in blood, there are the flame photometric method, the atomic absorption method, and the ion selective electrode method. In the present invention, a specimen obtained by collecting a small volume of blood from the finger and diluting the blood with a diluent solution is only about 150 μL, and it is preferable that measurement of a normal component homeostatically present in blood can be performed with a small volume of several μl because 10 or more items of biochemical components and immunological test items are measured. In addition, since it is necessary to analyze a large number of specimens, it is preferable that application thereof to a commercially available biochemical/automated immunoassay analyzer is possible.

[Volume of Diluent Solution and Dilution Factor]

In a case of testing a specific organ or a specific disease such as liver function, renal function, metabolism, and the like as a blood test, analysis of a plurality of target components to be measured is generally performed at the same time in order to perform a prediction and the like of a state of the organ, a lifestyle habit, and the like by obtaining information of the plurality of target components to be measured which are specific to the organ or the disease. For example, in order to test the state of a liver, generally, a concentration of various components in the blood such as ALT (alanine transaminase), AST (aspartate aminotransferase), γ-GTP (γ-glutamyl transpeptidase), ALP (alkaline phosphatase), total bilirubin, total protein, and albumins is measured. As above, in order to measure the plurality of target components from one blood sample, a certain volume of diluted blood is required in a case of considering a possibility of measuring again. Accordingly, regarding a diluent solution for diluting the collected blood, it is important that a certain volume thereof is secured. A volume of the diluent solution in the kit is preferably 20 times or less a volume of blood plasma (that is, a dilution factor is 20 times or less a volume of blood plasma), and is more preferably 15 times or less. For example, in a case where a volume of blood collection is 50 μL, a volume of blood plasma can be calculated as 28 μL, and in a case where the diluent solution is 360 μL, a dilution factor is 14. In a case where a ratio of blood cells to blood plasma is 50/50, a dilution factor in a case of using a blood sample as a standard can be approximately calculated by setting a dilution factor 50/(50+50) in a case of using blood plasma as standard. A volume of the diluent solution of the kit is preferably 10 times or less with respect to a volume of a blood sample (that is, a dilution factor is 10 times or less a volume of a blood sample), and more preferably 7.5 times or less. That is, the present invention provides the above-described blood test kit in which a volume of the diluent solution is 7.5 times or less a volume of a blood sample, as one embodiment.

[Separating Instrument for Separating and Recovering Blood Plasma From Diluted Blood Sample]

There is a possibility that a blood sample collected by the kit of the present invention is left alone for a long period of time in a diluted state before performing the analysis. During the time, for example, red blood cells are hemolyzed, which leads to the release of substances, enzymes, and the like which are present in the blood cells into the blood plasma or serum, and therefore a test result is affected thereby. Furthermore, there is a possibility that an absorption amount of the released hemoglobin affects a case of measuring an amount of a component to be analyzed with light information such as the optical absorption of the component to be analyzed, and the like. Therefore, it is preferable that the hemolysis is prevented. Accordingly, an embodiment in which the kit includes a separating instrument for separating and recovering blood plasma from a diluted blood sample is preferable. A preferred example of the separating instrument is a separation membrane. It is possible to use the separation membrane such that blood cells are separated and blood plasma components are recovered by applying pressure to the diluent solution of a blood sample, trapping the blood cell components with the separation membrane, and allowing the blood plasma components to pass through the separation membrane. In this case, it is preferable that an anticoagulant is used. In addition, in order to ensure the accuracy of measurement, it is preferable that backflow of the blood plasma passed through the separation membrane to the blood cells side does not occur. Therefore, specifically, the kit can include a backflow prevention means described in JP2003-270239A as a constituent component.

[Member and Elution From Member]

In the kit of the present invention, an amount of a normal component homeostatically present in blood, which is derived from the member of the blood kit and may be contained in the diluent solution is defined. It is possible to obtain an amount which may be contained in the diluent solution by actually exposing a target member to the diluent solution of an appropriate amount for a certain time, and then measuring an amount of a normal component which is derived from the member and becomes to be contained in the diluent solution. An amount of a normal component which is derived from the member is not particularly limited as long as it is an amount with which the analysis of a concentration of a target component is performed at high accuracy, and by which the measurement of a dilution ratio of a blood sample is not affected greatly. Specifically, an amount of a normal component homeostatically present in blood, which is derived from the member is 0.5% by mass or less, preferably 0.4% by weight or less, and more preferably 0.3% by weight or less with respect to the amount of the diluent solution. An amount of a normal component homeostatically present in blood, which is derived from the member of the blood kit and may be contained in the diluent solution is preferably small, and a lower limit value thereof is not particularly limited.

In the blood test kit, a fiber lot is generally used for an aspirator for collecting blood, and a sodium salt of ethylenediaminetetraacetic acid (EDTA) is used as an anticoagulant in this fiber lot. In addition, a glass filter is used as an instrument for separating and recovering blood plasma, in which a small amount of sodium ions such as soda glass and sodium carbonate is contained. Soda glass is obtained by mixing and melting quartz sand ($SiO_2$), sodium carbonate ($Na_2CO_3$), and calcium carbonate ($CaCO_3$). In a case where a material of the gasket for holding the glass filter and the sealing instrument for keeping the stored blood plasma in the second storing instrument is made of rubber, there is a case where a small amount of sodium ions is contained as a residue from NaOH cleaning for deproteinization, a release agent (mixture of sodium nitrate, sodium nitrite, and the like) which is used for molding, and the like. In a member which is a plastic (resin) molded product, a small amount of Na may be contained on the surface thereof in some cases. This is because, as metal elements in the release agent used for resin molding, sodium is contained together with tin, zinc, calcium, and the like.

It is presumed that these are mixed into the diluent solution as sodium ions derived from the kit. According to the examination by the inventors of the present invention, by setting an amount of a normal component homeostatically present in blood (preferably sodium ions or chloride ions), which is derived from the kit and may be actually contained in the diluent solution, to be sufficiently small, specifically, by setting a concentration thereof in the diluent solution to be 0.5% by weight or less, it was found that a high level of reproducibility and high accuracy can be obtained in a case where a volume of blood collection is 50 µL or more (a dilution factor estimated is 15 or smaller). In addition, in this case, in a case where an amount of sodium ions eluted into the diluent solution (an amount of sodium ions not derived from blood, that is, a contamination component) is preferably ±2% or smaller with respect to the amount of sodium ions in blood plasma, it is possible to maintain the calculation of a dilution factor at high accuracy.

The blood test kit of the present invention includes at least one member selected from the group consisting of a blood collection instrument for collection blood, a first storing instrument in which the diluent solution is stored, a separating instrument for separating and recovering blood plasma from the blood sample diluted with the diluent solution, a holding instrument for holding the separating instrument, a second storing instrument for storing the recovered blood plasma, and a sealing instrument for keeping the stored blood plasma in the second storing instrument. As the example of the blood test kit of the present invention, the kit can include a diluent solution for diluting components in a blood sample, a first storing instrument in which the diluent solution is stored, a separating instrument for separating and recovering blood plasma from the blood sample diluted with the diluent solution, a holding instrument for holding the separating instrument, a second storing instrument for storing the recovered blood plasma, a sealing instrument for keeping the blood plasma in the second storing instrument, a needle or a lancet for pricking the skin to allow blood to flow out of the skin, a strip of bandage or a sterile swab to be put on the wound (for example, nonwoven fabrics impregnated with isopropanol (70% isopropanol and the like), ethanol, or the like), an instruction manual, and the like. As the separating instrument for recovering blood plasma components from the diluted blood sample, an aspect of the separation membrane is preferable, and a filter having fine pores capable of separating blood cell components is more preferable.

Regarding the first storing instrument and the second storing instrument, one instrument may be used as both the first storing instrument and the second storing instrument, or an embodiment in which instruments are provided separately may be used. The first storing instrument and the second storing instrument are preferably made of a transparent material such that a patient or a measurer who performs measurement of a dilution factor and analysis of a target component to be analyzed can check a diluent solution in the storing instrument, by which the blood is diluted.

As the holding instrument for holding the separating instrument, an aspect of a gasket is preferable. In addition, as the sealing instrument, in a case where the storing instrument is an instrument having a tubular shape, and the like, it is possible to use a cap capable of being used as a lid for the opening, a lid having a helical groove, a rubber closure, and the like.

With the above configuration, by imparting the function of separating blood plasma from blood cells to the container in which the blood is mixed with the diluent solution immediately after diluting the blood with the diluent solution, it is possible to eliminate the influence on the stability of the blood components and the variation of the components due to hemolysis, and to impart the stability to the specimen after blood collection.

The kit of the present invention is capable of realizing a method in which a target component to be analyzed can be analyzed at high measurement accuracy even with a volume of blood collection of 100 µL or less, and is preferably a kit including an instruction manual in which information that measurement can be accurately performed even with a small volume of blood collection of 100 µL or less, and the like is described for a patient.

[Specific Example of Kit]

Figure 1:
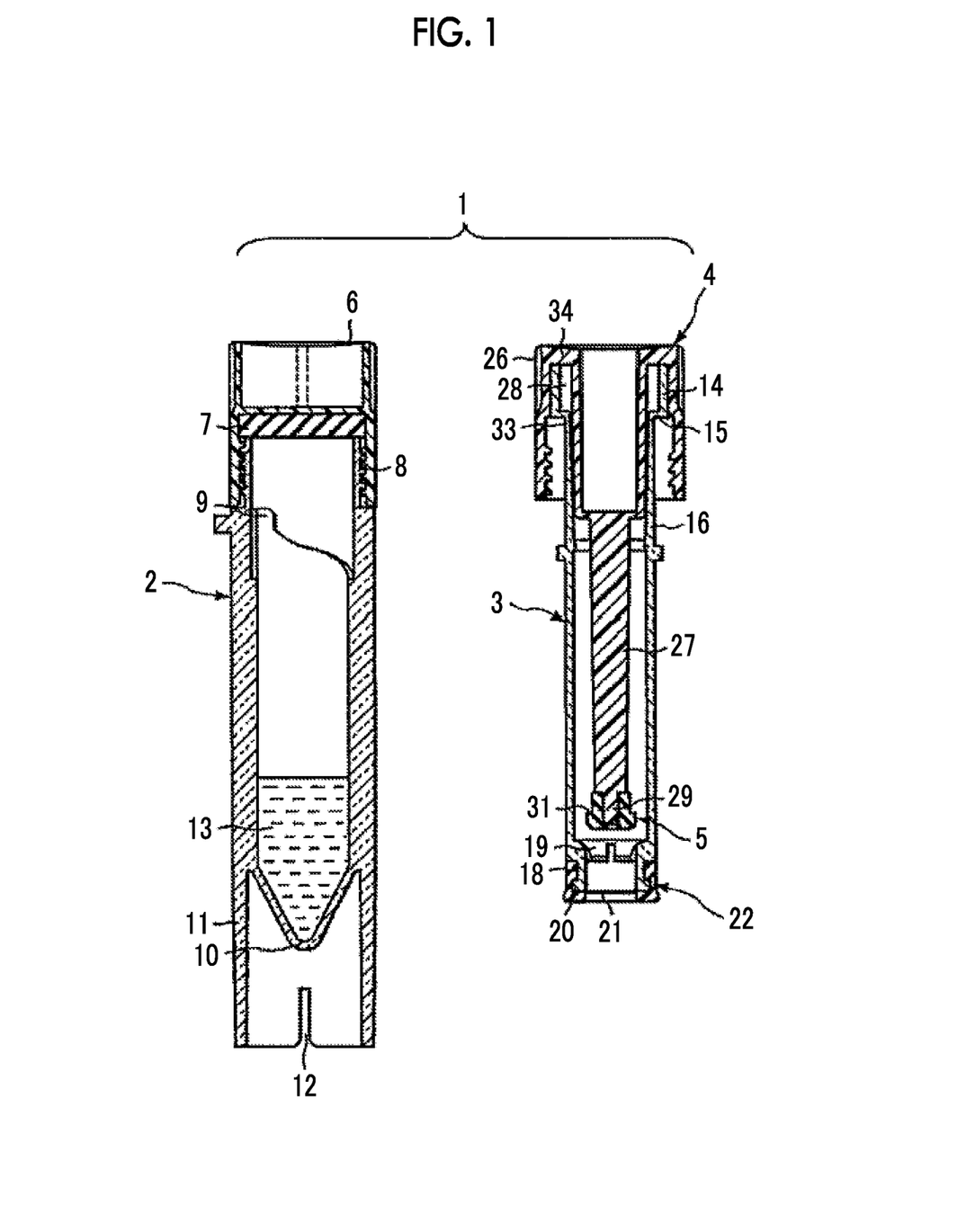
FIG. 1 is a cross sectional diagram of a blood test kit according to an embodiment of the present invention.

In one preferred embodiment, the kit includes the diluent solution, the first storing instrument in which the diluent solution is stored (which also may be a storing instrument for storing a diluted blood sample), the separating instrument for separating and recovering blood plasma from a blood sample diluted with the diluent solution, the holding instrument for holding the separating instrument, the second storing instrument for storing the recovered blood plasma, and the sealing instrument for keeping the stored blood plasma in the second storing instrument. As specific examples of the instruments, it is possible to use instruments described in FIG. 1 to FIG. 13 of JP3597827B. FIG. 1 of JP3597827B is incorporated as FIG. 1 of the present application.

A blood separating instrument 1 includes a blood collection container 2 (storing instrument in which a diluent solution is stored, which may be referred to as the first storing instrument in some cases. This is a storing instrument for storing a diluted blood sample), a tubular body 3 capable of being to fit into the blood collection container 2 so as to be inserted (second storing instrument for storing recovered blood plasma), a cap piston 4 capable of being capped on the tubular body 3, and a sealing lid 5 (sealing instrument) provided at a lower end of the cap piston 4. Before use, an upper end opening portion of the blood collection container 2 is sealed by a cap 6 via a packing 7, as shown in FIG. 1. The storing instrument for storing a diluted blood sample of the present invention corresponds to a combination of the blood collection container 2 and the tubular body 3 in the configuration of FIG. 1. That is, the storing instrument for storing a diluted blood sample may be one or a combination of two or more thereof.

The blood collection container 2 is made of a transparent material and has a cylindrical shape. At the upper end portion thereof, a screw portion 8 is formed on the outer surface, and a locking portion 9 is protruded toward the inner surface. In addition, at a lower end portion of the blood collection container 2, a bottom portion 10 having an inverted conical shape is formed, and a cylindrical leg portion 11 is formed around the bottom portion 10. The leg portion 11 has the same outer diameter as a sample cup used at the time of an analytical test of blood, and at positions opposite to the lower end thereof, slit grooves 12 are preferably formed in a vertical direction, respectively. Furthermore, a predetermined volume, for example, 500 mm$^3$ of a diluent solution 13 may be put in the blood collection container 2 in advance, as shown in FIG. 1.

The tubular body 3 is made of a transparent material and has a cylindrical shape, and at an upper end portion thereof, an expanded diameter section 14 is formed. The expanded diameter section 14 is connected to a main body portion 16 via a thin portion 15. A reduced diameter section 18 is formed at the lower end portion of the tubular body 3, and a protruded locking portion 19 is formed on the inner surface of the reduced diameter section 18. Furthermore, at a lower end portion of the reduced diameter section 18, an outer flange portion 20 (holding instrument) is formed, a lower end opening portion of the outer flange portion 20 is covered with a filtration membrane 21 (separating instrument), and the filtration membrane 21 allows blood plasma in the blood to pass through and prevents passage of the blood cells.

A cover 22 made of silicone rubber is attached to the outer periphery of the reduced diameter section 18 (FIG. 1).

The cap piston 4 is constituted by a substantially cylindrical knob portion 26 and a mandrel portion 27 concentric with the knob portion 26 and extending downward. At an inner upper end portion of the knob portion 26, a cylindrical space 28 into which the expanded diameter section 14 of the tubular body 3 is capable of being fitted to be inserted is formed, and the knob portion is threaded in a lower portion into which a screw can screw. The mandrel portion 27 has a lower end portion 29 formed in a pin shape, and the sealing lid 5 is detachably provided on the lower end portion 29 (refer to FIG. 1). The sealing lid 5 is made of silicone rubber.

Specifically, the operation of separating and recovering blood plasma from a blood sample is performed as below. The collected blood is added to the blood collection container 2 storing the diluent solution, and then the blood and the diluent solution are thoroughly shaken to be mixed while noting that bubbles are not generated by holding an upper portion of the blood collection container 2. Next, the tubular body 3 holding the filtration membrane 21 (for preventing solution leakage due to infiltration into a side surface of a cylinder at the time of separating blood plasma from blood cells) is inserted into the blood collection container 2 such that the filtration membrane faces downward, and the filtration membrane is slowly pushed into the bottom of the blood collection container 2 at a constant speed. At this time, the blood plasma passes through the filtration membrane of the tubular body 3 and then floats on the upper portion, and the blood cells remain on the lower portion of the blood collection container 2. Thereafter, the cap piston 4 is slowly pushed into the tubular body 3, by which mixing of the blood plasma with the blood cells due to backflow is prevented by the sealing lid 5.

A method for separating blood by the instruments described above is described in detail in paragraphs 0023 to 0026 and FIG. 12 and FIG. 13 of JP3597827B, the contents of which are incorporated in the present specification.

The number of various components contained in the blood test kit of the present invention is not particularly limited, and each component may be one, or there may be a plurality of, for example, 2 or more thereof.

The material of the member included in the blood test kit of the present invention is preferably a synthetic resin from the viewpoints of difficulty in breakage, sanitation, price, and the like. Examples thereof include polyethylene, polypropylene, polyvinyl chloride, polyvinylidene chloride, polystyrene, polyvinyl acetate, polyurethane, polyethylene terephthalate, polylactic acid, acrylonitrile butadiene styrene resin (ABS resin), acrylonitrile styrene resin (AS resin), acrylic resin (PMMA), polycarbonate, silicone resin, and the like.

The blood test kit of the present invention can provide all members in an aspect in which the members are stored in the storing container.

[2] Method for Manufacturing Kit and Member

The present invention further provides a method for manufacturing the above-described kit and member. The manufacturing method of the present invention includes a step of washing the member under a condition effective for removing a normal component which is homeostatically present in blood.

[Step of Washing Member]

The material of the member used for the blood test kit of the present invention is plastic, glass, or rubber, but the inventors of the present invention have found that in a step of manufacturing the blood test kit including a step of manufacturing the member, a normal component homeostatically present in blood, which may be eluted from this member can be effectively removed by a predetermined method.

The condition effective for removing a normal component which is homeostatically present in blood is specifically a step of washing a target member with pure water having an electric conductivity of 1 μS/cm or less, and is preferably a step of showering a target member with pure water having an electric conductivity of 1 μS/cm or less. The inventors of the present invention have found that a concentration of elution can be lowered to 0.5% by weight or less with respect to the diluent solution by performing the washing through such steps.

Also from the viewpoint of washing the member, a normal component homeostatically present in blood is preferably sodium ions or chloride ions which are present at high concentration in a small volume of blood. For example, it is easy to remove sodium ions or chloride ions to a level that does not cause problems in performing the analysis compared to calcium ions that are one-fifteenth or magnesium ions that are one-eightieth in average value with respect to sodium ions. In order to remove calcium ions or magnesium ions, it is preferable to wash with high-level pure water (for example, 0.1 μS/cm or less) or ultrapure water (0.06 μS/cm or less), but this is disadvantageous in terms of cost.

[3] Others

The present invention further provides a blood analysis method in which the kit of the configuration described in [1] of the present specification is used. The blood analysis method includes an aspect which is a medical practice (practice performed by a doctor) for humans and an aspect which is not a medical practice for humans (for example, an aspect in which a person who performs blood collection is a patient himself and an analyzer is a person other than a doctor, an aspect for non-human animals, and the like). The blood analysis method of the present invention may be performed by the self-blood collection in which a subject to be tested collects blood by himself, or may be performed by the general blood collection in which a qualified person such as a doctor collects blood using a syringe. As a preferred embodiment, a patient pricks the fingertip and the like by himself using an instrument equipped with a small blade such as a lancet, and then collects blood flowing out of the skin.

A biological specimen which is a target to be analyzed using the kit of the present invention is blood, and the blood is a concept of including serum or blood plasma. The origin of blood is not limited to humans, and may be mammals, birds, fish, and the like which are animals other than humans (non-human animals). Examples of the animals other than humans include horses, cows, pigs, sheep, goats, dogs, cats, mice, bears, pandas, and the like. The origin of a biological specimen is preferably humans.

In a case of performing the analysis using the kit of the present invention, the target component to be analyzed is not limited and any substance contained in blood is a target. Examples thereof include biochemical test items in blood used for clinical diagnosis, markers of various diseases such as tumor markers and hepatitis markers, and the like, and include proteins, sugars, lipids, low molecular weight compounds, and the like. In addition, not only a concentration of a substance is measured, but also an activity of a substance having an activity such as an enzyme is targeted. Analysis of each target component can be carried out by a known method.

EXAMPLE

Hereinafter, examples and comparative examples of the present invention will be explained.

Figure 2:
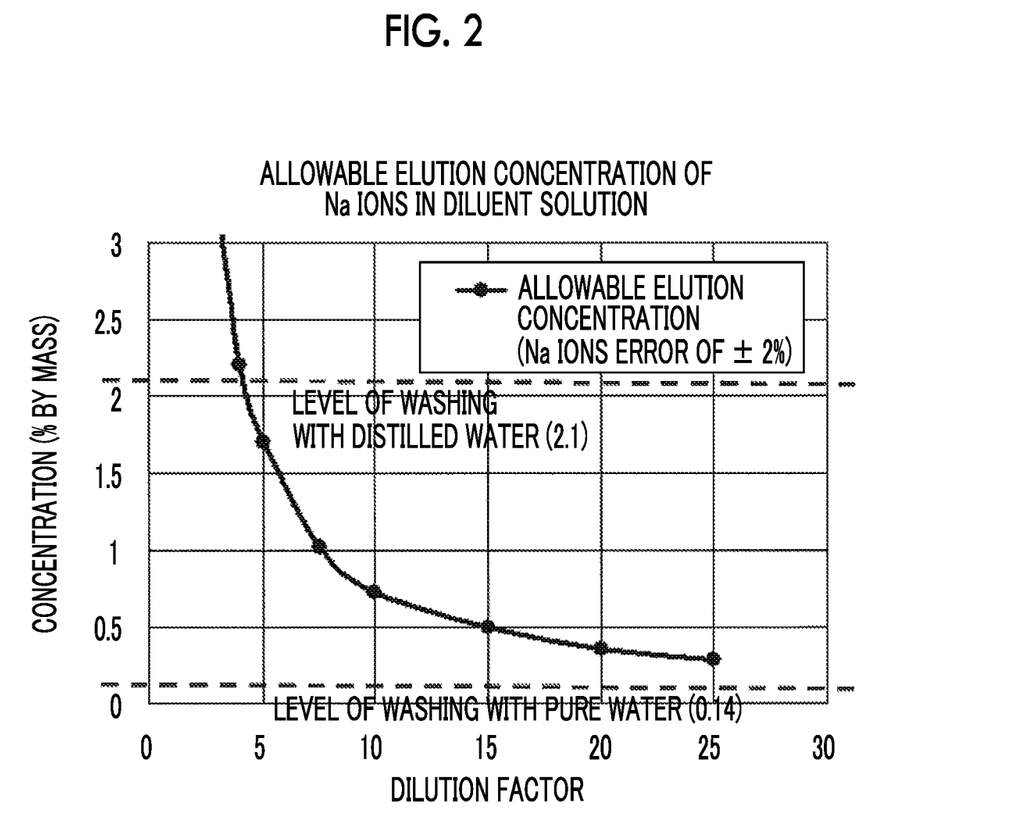
FIG. 2 illustrates an example of a result of calculation of an allowable elution concentration (% by weight with respect to a diluent solution) of sodium ions in the diluent solution.

By using sodium ions which are normal component homeostatically present in blood as a standard substance, and setting an average value of a concentration of sodium ions to 142 mmol/L, it is possible to dilute a blood sample with a diluent solution and to calculate an average value of sodium ions present in blood plasma which is separated and recovered. Meanwhile, it has been found that in a case where an amount of sodium ions in the diluent solution, which are derived from a member (an amount of sodium ions not derived from blood, that is, a contamination component) is preferably ±2% or smaller with respect to the amount of sodium ions in blood plasma, it is possible to maintain calculation of a dilution factor at high accuracy. Therefore, an allowable elution concentration of sodium ions in the diluent solution (% by weight with respect to the diluent solution) is calculated with the diluent solution of 300 µL and a dilution factor in a range of 3 to 25. The results are shown in FIG. 2.

For example, in a case of a dilution factor of 5, an allowable concentration of sodium ions in the diluent solution, which are derived from a member is 1.7% by mass, that is, an allowable elution amount of sodium ions with respect to the diluent solution of 360 µL is ±6.1 µg. In addition, in a case of a dilution factor of 20, an allowable elution concentration of sodium ions in the diluent solution is 0.35% by mass, that is, ±1.3 µg with respect to the diluent solution of 360 µL. Base on this, it is understood that as a dilution factor becomes higher, an allowable elution amount of sodium ions eluted into the diluent solution becomes rapidly high, and therefore the accuracy of a dilution factor decreases due to an elution amount in the diluent solution of a smaller volume as contamination.

Reference Example 1

1. Washing Member and Preparation of Diluent Solution

DEMECAL blood test kit (Leisure, Inc.) was used. In this case, a bottle that is a member of the blood test kit (first storing instrument for storing a diluent solution), a filter (separating instrument for separating and recovering blood plasma from a blood sample diluted with the diluent solution), and a gasket (holding instrument for holding the separating instrument) were subjected to no washing, tap water washing, distilled water washing, and pure water washing (electric conductivity of 1 µS/cm) in advance. Thereafter, 360 µL of Diluent Solution 1 prepared as below was added to the bottle, the filter held by the gasket was pushed into the bottle to filter the diluent solution, and an amount of sodium ions in the solution passed through the filter was measured. The washing was performed in a manner of showering the member with water.

(Composition of Diluent Solution)

A diluent solution was prepared with the following composition. As osmotic pressure, a value measured by using OSMOATAT OM-6040 (manufactured by ARKRAY, Inc.) is shown. A unit of the osmotic pressure is an osmotic pressure that 1 kg of water of a solution has, and indicates millimoles of ions.

HEPES 50 mmol/L
2-amino-2-methyl-1-propanol (AMP) 50 mmol/L
D-Mannitol 284 mmol/L
Lithium chloride 1 mmol/L
EDTA-2K 0.8 mmol/L
PALP (pyridoxal phosphate) 0.05 mmol/L
Thiabendazole 0.0001% by mass
Amikacin sulfate 0.0003% by mass
Kanamycin sulfate 0.0005% by mass
Meropenem trihydrate 0.0005% by mass
Osmotic pressure 355 mOsm/kg
pH 7.4

2. Measurement of Concentration of Sodium

A concentration of sodium was measured with respect to each diluent solution prepared in 1. The measurement was carried out by the enzyme activity method utilizing that β-galactosidase is activated by sodium, which is that each concentration of sodium in the diluent solution and β-galactosidase activity are in a proportional relationship. Specifically, after diluting the dilution solution of the blood five times by using purified water not containing sodium ions, 3 µL was weighed, 52 µL of a first reagent prepared as described below was added thereto, and then heated at 37° C. for 5 minutes. 26 µL of a second reagent prepared as described below was added thereto, and the change in absorbance was obtained by measuring an absorbance during 1 minute at a main wavelength of 410 nm and a complementary wavelength of 658 nm by using JCA-BM6050-type automatic biochemistry analyzer (manufactured by JEOL Ltd.). The concentration of sodium was measured from a calibration curve prepared in advance.

(Preparation of Reagent for Measuring Sodium)

A reagent for measuring sodium having the following composition was prepared.

First Reagent
HEPES/LiOH (pH 8.0) 100 mmol/L
D-Mannitol 60 mmol/L
N-acetylcysteine 30 mmol/L
Magnesium sulfate 1.52 mmol/L
β-galactosidase 1.1 kU/L
TRITON X-100 0.05% by mass Second Reagent
HEPES/LiOH (pH 8.0) 100 mmol/L
o-Nitrophenyl β-D-galactopyranoside 15 mmol/L Each of five supernatants after separation were prepared for each washing, and an average value of a concentration of Na ions eluted into the diluent solution, and CV (coefficient of variation) (%), a coefficient of variation, which is a measure of the variation were obtained. The results are shown in Table 1.

TABLE 1

| Washing method | Diluent Solution 1 (µL) | Average value (% by weight) of concentration of Na ions eluted into diluent solution | CV (%) of concentration of Na ions eluted into diluent solution | Note |
|---|---|---|---|---|
| Pure water washing | 360 | 0.14 | 2.4 | Example |
| Distilled water washing | 360 | 2.1 | 2.5 | Comparative Example |
| Tap water washing | 360 | 4.3 | 2.2 | Comparative Example |
| No washing | 360 | 4.3 | 3.3 | Comparative Example |

In FIG. 2, a concentration level of sodium ions eluted into the diluent solution, in the diluent solution is illustrated by a dotted line in a case of subjecting the members (bottle, gasket, filter) of the blood test kit to pure water washing and tap water washing.

Based on the results of FIG. 2 and Table 1, it was found that by subjecting the bottle, the gasket, and the filter which are the members of the blood test kit to pure water washing in advance in a case where sodium ions which are components homeostatically present blood are used as a standard substance, it is possible to lower a concentration of sodium eluted into the diluent solution, in the diluent solution down to about 0.14% by weight in average value, and that an allowable elution concentration of sodium ions in the diluent solution, which is for calculating a dilution factor at high accuracy is sufficiently clear in a wide range of a high dilution factor. The experiment was carried out using lithium ions contained in the diluent solution which substantially does not contain sodium ions as a standard substance, but irrespective of the presence or absence of lithium ions, if substantially no sodium ions are contained, the same result is, needless to say, obtained.

Example 1

(Measurement of Lithium Ions in Diluent Solution)

A concentration of lithium ions in each diluent solution prepared in Reference Example 1 was measured as below.

Measurement of lithium ions added to the diluent solution was carried out by the chelate colorimetric method (halogenated porphyrin chelating method: perfluoro-5,10,15,20-tetraphenyl-21H,23H-porphyrin). Specifically, after diluting the dilution solution of the blood 4.5 times by using purified water not containing lithium ions, 5 µL was weighed, 55 µL of a third reagent prepared as described below was added thereto, and then heated at 37° C. for 10 minutes. An absorbance was measured at a main wavelength of 545 nm and a complementary wavelength of 596 nm by using JCA-BM6050-type automatic biochemistry analyzer (manufactured by JEOL Ltd.). It was possible to measure the concentration of lithium ions from a calibration curve prepared in advance.

(Preparation of Reagent for Measuring Lithium Ions)

A reagent for measuring lithium ions having the following composition was prepared.

Third Reagent
Perfluoro-5,10,15,20-tetraphenyl-21H,23H-porphyrin 0.05% by mass
Dimethyl sulfoxide 5% by mass
Triethanolamine 2% by mass
Polyethylene glycol-t-octylphenyl ether 2% by mass
Sodium dodecyl sulfate 2% by mass A method for obtaining a dilution factor of blood plasma in blood and a calculation formula are shown in below.
A: Absorbance in a case of coloring a buffer solution
B: Absorbance change after adding blood plasma
C: Absorbance at a median value of 142 mmol/L of blood plasma sodium
D: Absorbance at a concentration of sodium ions after diluting blood plasma
X: Dilution factor of blood plasma For obtaining a dilution factor from blood plasma of a buffer solution, a relationship in Formula (1) was used.

$$X=[\{(A/B)^2+(C/D)^2\}/2]^{1/2}$$

It is understood that the square root of the sum of squares of information on the diluent solution of lithium ions as an internal standard substance, which are present in the diluent solution and information on sodium ions as a normal component homeostatically present in blood is obtained as shown in Formula (1), and from both information of the internal standard substance and the normal component homeostatically present in blood, it is possible to obtain a dilution ratio, and that the measurement of a dilution ratio at high accuracy is possible by using the kit in which an elution amount of the normal component homeostatically present in blood is defined.

Example 2

After informed consent was obtained from a volunteer patient, a blood volume of 10 µL collected from the vein by a syringe was recovered with a sponge, the blood recovered by the sponge was mixed with the diluent solution prepared with the kit using the bottle, the filter, the gasket, which were subjected to pure water washing in advance in the same manner as in Reference Example 1, and then blood cells were separated through a filter. A concentration of sodium ions in the diluted blood plasma after separating the blood cells obtained as above was measured in the same manner as in Reference Example 1. In addition, a concentration of total protein in the same diluted blood plasma was measured in a method described below.

(Measurement of Concentration of Total Protein in Diluted Blood Plasma)

Measurement using the biuret method as the measurement principle was performed. Biuret reagent: 3.0 mmol/L, copper sulfate 400 µl, potassium sodium tartrate 21.3 mmol/L, and NaOH 0.75 mmol/L were prepared and mixed with the diluted blood plasma. After mixing, the mixture was left alone at 37° C. for 10 minutes, and it was waited until a complex exhibiting blue-violet color of 540 to 560 nm due to protein and copper ions in blood plasma was formed under an alkaline environment, the absorbance was measured at 545 nm, and therefore, a concentration of total protein in the diluted blood plasma after separating blood cells was quantitatively determined using a calibration curve obtained from the absorbance of a standard solution.

When a dilution factor of each blood plasma was calculated based on the measurement values of a concertation of sodium ions and a concertation of total protein, and a concentration of a normal component of a concertation of sodium ions homeostatically present in blood plasma and a concertation of total protein, which were measured as described above, the matched dilution factors were obtained. Accordingly, it was understood that the analysis of a concentration of a target component in a blood sample in which an amount of a normal component derived from the member is defined, is normally performed by obtaining a dilution factor using at least one homeostatic substance different from sodium ions, in addition to a concentration of sodium ions, and it was understood that the verifying of the measurement result is possible.

EXPLANATION OF REFERENCES

1: blood separating instrument
2: blood collection container
3: tubular body
4: cap piston
5: sealing lid
6: cap
7: packing
8: screw portion
9: locking portion
10: bottom portion
11: leg portion
12: slit grooves
13: diluent solution
14: expanded diameter section
15: thin wall portion
16: main body portion
18: reduced diameter section
19: protruded locking portion
20: outer flange portion
21: filtration membrane
22: cover
26: knob portion
27: mandrel portion
28: space
29: lower end portion
31: level difference portion
33: upper end portion
34: top portion

What is claimed is:

1. A method for manufacturing a blood test kit for analyzing a concentration of a target component in a blood sample by using a normal component homeostatically present in blood, the kit comprising:
a diluent solution for diluting the blood sample; and
a member selected from the group consisting of a first storing instrument in which the diluent solution is stored, a separating instrument for separating and recovering blood plasma from the blood sample diluted with the diluent solution, a holding instrument for holding the separating instrument, a second storing instrument for storing the recovered blood plasma, and a sealing instrument for keeping the stored blood plasma in the second storing instrument,
wherein the normal component(s) homeostatically present in blood is sodium ions or chloride ions, and another normal component homeostatically present in blood, the another normal component is total protein or albumins, and
an amount of sodium ions or chloride ions which is derived from the member and is contained in the diluent solution is defined,
wherein an amount of the normal component which is derived from the member and is contained in the diluent solution is 0.14% by mass or less with respect to the amount of the diluent solution, the method comprising:
a step of preparing the diluent solution for diluting the blood sample, the first storing instrument, the separating instrument for separating and recovering blood plasma from the blood sample diluted with the diluent solution, the holding instrument for holding the separating instrument, the second storing instrument for storing the recovered blood plasma, and the sealing instrument for keeping the stored blood plasma in the second storing instrument,
a step of washing the first storing instrument, the separating instrument, and the holding instrument, under a condition effective for removing the normal component homeostatically present in blood,
a step of storing the diluent solution in the washed first storing instrument, and
a step of composing the kit with the first storing instrument in which the diluent solution is stored, the washed separating instrument, the washed holding instrument, the second storing instrument, and the sealing instrument.

2. The method according to claim 1,
wherein a volume of the diluent solution is 15 times or smaller a volume of blood plasma.

3. The method according to claim 1,
wherein the blood test kit has a separating instrument for recovering blood plasma from the blood sample diluted with the diluent solution.

4. The method according to claim 1,
wherein the diluent solution does not contain the normal component homeostatically present in blood.

5. The method according to claim 1,
wherein the diluent solution contains an amino alcohol compound selected from the group consisting of 2-amino-2-methyl-1-propanol, 2-ethylaminoethanol, N-methyl-D-glucamine, diethanolamine, and triethanolamine, and contains a buffering agent selected from the group consisting of 2-[4-(2-hydroxyethyl)-1-piperazinyl]ethanesulfonic acid also called HEPES, N-tris(hydroxymethyl)methyl-2-aminoethanesulfonic acid also called TES, 3-morpholinopropanesulfonic acid also called MOPS, and N,N-bis(2-hydroxyethyl)-2-aminoethanesulfonic acid also called BES.

6. The method according to claim 1,
wherein the diluent solution further contains a normal component not present in blood.

7. The method according to claim 6,
wherein the normal component not present in blood is lithium ions or glycerol 3-phosphate.

8. The manufacturing method according to claim 1,
wherein the condition is use of water having an electric conductivity of 1 μS/cm or less.

* * * * *